United States Patent [19]

Burkhart

[11] 3,996,119

[45] Dec. 7, 1976

[54] METHOD FOR ELECTROLYTIC ETCHING OF GRAY IRONS WITH STEAD'S REAGENT

[75] Inventor: Russell D. Burkhart, Black Hawk County, Iowa

[73] Assignee: Deere & Company, Moline, Ill.

[22] Filed: Feb. 2, 1976

[21] Appl. No.: 654,417

[52] U.S. Cl. .................... 204/129.85; 204/129.95
[51] Int. Cl.$^2$ ........................................ C25F 3/06
[58] Field of Search ...... 204/129.8, 129.85, 129.95

[56] References Cited
UNITED STATES PATENTS

| | | | |
|---|---|---|---|
| 2,516,105 | 7/1950 | Mateosian | 204/129.85 |
| 2,752,304 | 6/1956 | Darmois et al. | 204/129.85 |

*Primary Examiner*—T. M. Tufariello

[57] ABSTRACT

A process for electrolytically etching phosphorus bearing gray irons using Stead's reagent is provided. Stead's reagent, which is used as the electrolyte in the etching process is composed of 1.2% cupric chloride, 4.6% magnesium chloride, 2.8% HCl and 91.4% ethanol. The time required for etching both low and high phosphorus bearing irons is reduced to 90 seconds or less and clear grain cell definition in both high and low phosphorus-containing gray iron is achieved by using Stead's reagent as the electrolyte in an electrolytic cell wherein the specimen to be etched operates as the anode.

7 Claims, No Drawings

METHOD FOR ELECTROLYTIC ETCHING OF GRAY IRONS WITH STEAD'S REAGENT

BACKGROUND OF THE INVENTION

The science of metallography is essentially the study of the structural characteristics or constitution of a metal or an alloy in relation to its physical and mechanical properties. One important phase of this study is known as macroscopic examination and involves the visual observation of the rather gross structural details of a metal, either by the unaided eye or with the aid of a low-power microscope or binocular. Because the attending magnifications are of low order, usually under 10×, macroscopic observations are somewhat limited as to the kind of metallurgical data revealed. However, macroscopic examinations, when appropriately carried out, are of considerable importance in many instances with some metallic characteristics preferably determined by such studies.

Another phase of metallography deals with the microscopic examination of a prepared metal specimen, employing magnifications with the optical microscope of from 100× to as high as 500×. Such microscopic studies are of much broader scope than are macroscopic examinations, and under appropriate conditions of observation there will be revealed to the trained metallographer an abundance of constitutional information concerning the metal or alloy under investigation, such as, for example, grain size; the size, shape, and distribution of secondary phases and nonmetallic inclusions; and segregation and other heterogeneous conditions — all of which profoundly influence the mechanical properties and behavior characteristics of the metal. When these and other constitutional features are determined by microscopic examination and the extent to which they exist in the microstructure is known, it is then possible to predict with considerable accuracy the expected behavior of the metal when used for a specific purpose. Of equal importance is the fact that within limits there is reflected in the microstructure an almost complete history of the mechanical and thermal treatment that a metal has received.

The surface of the metal which is to be so examined is first prepared according to more or less rigid and precise procedures. With the use of the modern metallurgical microscope and precision optical parts where the obtainable resolution may be as great as a fraction of the wave length of light used to illuminate the specimen, it is evident that specimen preparation is of great importance. Improper preparation is likely to remove all-important inclusions, erode grain boundaries, or temper hardened steel specimens, ultimately producing a structure, superficially at least, which upon microscopic examination will appear entirely different from that which is truly representative and characteristic of the metal. Obviously, an examination of such a prepared specimen will lead only to erroneous interpretations and unreliable conclusions.

In general, specimen preparation procedure consists of first obtaining a flat, semipolished surface by various methods known to those skilled in the art, such as, chemical mechanical polishing and electro-mechanical polishing. These operations ultimately produce the flat, scratch-free, mirror like surface which is required before the specimen can be etched and the metallographic structure appropriately revealed.

Metallographic etching is then used to reveal particular structural characteristics of a metal that are not evident in the as-polished condition.

Two popular etching techniques known to those skilled in the art include chemical etching and electrolytic etching. Although the manipulations involved in etching a metallographic specimen are relatively simple to carry out, a certain amount of skill is required on the part of the technician to secure a satisfactory etched surface.

Perhaps the most important preliminary consideration in the procedure is the selection of an appropriate etching reagent from the many that are recommended for any given metal or alloy. This selection requires judgment and knowledge of the behavior of the various reagents when used under recommended conditions. A selected agent must be used for the specific purpose for which it was intended, and to secure the desired results, the directions pertaining to its use must be adhered to.

In the art of electrolytic or chemical etching, the selection of an appropriate etching reagent depends primarily upon the composition of the metal or alloy to be etched, the method of etching to be utilized and which constituents in the structure are to be revealed by etching. Thus each metal or alloy has a number of recommended etchants, the use of which is quite specific.

It is generally known to chemically etch phosphorus-containing gray irons, to reveal the grain cells, with Stead's reagent for both macroscopic and microscopic examination. Stead's reagent (which is composed of 1.2 weight percent cupic chloride, 4.6 weight percent magnesium chloride, 2.8 weight percent hydrochloric acid and 91.4 weight percent ethanol) selectively darkens low phosphorus regions in the iron, leaving high phosphorus regions (normally segregated at grain cell boundaries) unattached and light.

The technical literature indicates that chemical etching of gray irons with Stead's reagent requires immersion of the sample in the reagent for up to three hours. It has been found, however, that chemical etching of phosphorus-containing gray irons can be performed in much shorter times, e.g., from about 1 to about 5, generally about 3 to about 4 minutes. Although the reduced immersion times are of considerable significance in commercial foundry operations, there are a number of other problems with chemical etching of phosphorus-containing gray irons with Stead's reagent.

Chemical etching of phosphorus-containing gray irons with Stead's reagent has been found to be generally more successful when the gray iron has a high phosphorus content, e.g., about 0.5 to 0.6 weight percent or more. When the phosphorus content of the gray iron is low, e.g., about 0.06 weight percent or less, the etched surface has been often found to be obscure with relatively poor (if any) differentiation of the grain cells. The obscurity has been found to remain even with longer etching times of 10 to 15 minutes or more. In such cases, visual and microscopic observations of grain cell size and count are difficult, if not impossible, to perform and photographs and photomicrographs are also too obscure to be of value to the investigator. Although the problem is more acute with low phosphorus-containing gray irons, it often occurs also in the chemical etching of gray irons with intermediate (e.g., 0.07 to 0.15) and high (e.g., 0.16 and above) phosphorus-containing gray irons. Other types of chemical etching (e.g., heat tinting and deep acid etch) have also been found to be generally unsuitable for consistent clear and definite etching of the various phosphorus-containing gray irons.

OBJECTS AND SUMMARY OF THE INVENTION

It is therefore an object of this invention to provide a simple, direct, and rapid process for etching both low and high phosphorus irons.

It is also an object of this invention to provide an etching process which may be used to prepare low, intermediate and high phosphorus-containing gray irons for both microscopic and macroscopic examination.

A further object of the present invention is to provide an electrolytic etching process for electrolytically etching phosphorus-containing gray irons using Stead's reagent for both micro-and macroscopic examination.

These and other objects as well as the scope, nature, and utilization of the invention will be apparent to those skilled in the art from the following description and appended claims.

In one aspect of the present invention there is provided in a process of electrolytically etching phosphorus bearing gray irons to reveal surface structure with an electrolytic reagent, the improvement comprising utilizing Stead's reagent as the electrolytic reagent.

In another aspect of the present invention, there is provided a process for electrolytically etching phosphorus bearing gray irons which comprises immersing a phosphorus-containing gray iron sample in a bath of Stead's reagent, and passing a direct current through said bath between said sample and a cooperating electrode to electrolytically etch the surface of the sample sufficient for microscopic or macroscopic examination thereof.

The essence of the present invention is the discovery that the use of electrolytic etching techniques with Stead's reagent as the electrolyte achieves relatively rapid (e.g., 90seconds or less, generally 60seconds or less) etching of phosphorus-containing gray irons irrespective of the phosphorus content. Thus, even low phosphorus-containing (0.06 weight percent phosphorus or less) gray ironss are sufficiently etched in this short time span for visual or microscopic examination. The grain cells and grain boundaries are clearly delineated and photographs and photomicrographs are clear and definite. The process of the present invention thus provides a unique compatibility with the entire range of phosphorus contents found in gray irons.

The mechanism of electrolytically etching phosphorus-containing gray irons with Stead's reagent appears to be somewhat different from that of chemical etching with Stead's reagent. That is, chemical etching with Stead's reagent of phosphorus-containing gray irons depends on the presence of an iron phosphide eutectic composition (or "Steadite") which is precipitated in the grain boundary material surrounding the iron-carbon eutectic cells (e.g., austenite-graphite) formed during solidification of the iron. The Stead's reagent reacts with the Steadite in the grain boundaries and thus reveals the outline of the iron-carbon eutectic cells. This method is thus dependent on a well-defined cell pattern with grain boundary material containing sufficient iron phosphide. As noted in the literature, when phosphorus content increases (e.g., 0.5 weight percent or more), the grain cell differentiation becomes more difficult to assay.

The electrolytic etching method of the present invention, however, not only etches the Steadite present in the grain boundaries but also etches the difference in eutectic cell composition from the center of the cell to the grain boundary that also occurs in solidification of the iron. Thus, the entire surface of the sample is differentially etched and not just the grain boundary. Grain cell differentiation is thus possible for a wide phosphorus-content range of gray irons.

Another advantage of the process of the present invention is that the useful life of the Stead's reagent etching bath is substantially increased. When Stead's reagent is utilized in chemical etching, the reagent bath, after a period of time, tends to deposit metallic copper on the sample which masks the grain cell structure. This apparent exhaustion time of the reagent bath is substantially increased when the Stead's reagent is utilized in the electrolytic etching process of the present invention.

DESCRIPTION OF THE PREFERRED EMBODIMENTS

Stead's reagent as known in the art is a solution which is comprised of 10 grams of cupric chloride, 40 grams of magnesium chloride, 20 milliliters of hydrochloric acid and 1000 milliliters of ethanol which on a percent by weight basis is 1.2% cupric chloride, 4.6% magnesium chloride, 2.8% of a 40% aqueous solution of HCL at 20° C and 91.4% of a 99% solution of the ethanol at 20° C.

The reagent may be prepared by dissolving the magnesium chloride and cupric chloride in hydrochloric acid with the addition of the least amount of hot water necessary to effect solution (usually about 10 to 15 milliliters per liter of solution prepared) with the subsequent addition of the methanol.

The electrolytic etching process of this invention is successfully practiced on phosphorus-containing gray irons. The phosphorus content generally varies up to about 1 weight percent.

As utilized herein, the terms "low phosphorus-containing gray iron" refers to gray iron having a phosphorus content of about 0.06 weight percent or less, "intermediate phosphorus-containing gray iron" refers to a gray iron having a phosphorus content of from about 0.07 to about 0.15 weight percent and "high phosphorus-containing gray iron" refers to a gray iron having a phosphorus content of about 0.16 weight percent or more. Typical commercial low, intermediate and high phosphorus-containing gray irons contain about 0.03 to 0.04, 0.10 to 0.12 and 0.5 to 0.6, respectively, weight percent phosphorus.

Prior to electrolytic etching the specimen to be etched is prepared, usually by conventional polishing techniques such as chemical, mechanical, or any other polishing method known to those skilled in the art, to provide a flat and scratch-free surface.

It is generally considered good technique to wash the specimen surface thoroughly in a stream of warm water before etching, swab the surface with wet cotton, rinse in ethyl alcohol and dry the specimen in warm air, to ensure that the specimen surface is clean and free from tarnish and to ensure even and uniform wetting of the surface by the etching reagent.

When possible, the specimen should be of a size that is convenient and comfortable to handle. Specimens that have large surface areas will usually require prolonged polishing to produce a satisfactory surface whereas specimens that are small, unless mounted, will tend to rock on the emery papers during grinding, with resultant rounded edges and curved surfaces. A specimen of a size and shape easy to manipulate is approximately from ½ to ¾ inch across the polished surface, either round or square, and approximately ⅜ inch high. This relation between the breath and the height of the specimen will assist in maintaining a flat surface with the least amount of fatigue to the technician during subsequent grinding and polishing. The particular size or shape utilized may vary depending upon various factors as is well-known to the skilled artisan. If desired, the specimen may be mounted in a conventional manner for use in the electrolytic etching process.

The electrolytic method of etching of the present invention may be conducted in any known electrolytic etching apparatus and typically consists of placing a direct current through the bath of Stead's reagent wherein the specimen to be etched is usually made inn the anode and some insoluble material such as platinum or graphite cooperates as the cathode.

The process of the present invention can be performed using conventional electrolytic etching equipment. Typically, the direct current is applied using standard 6 or 12 volt dry cell batteries although the voltage may be higher or lower as known to the skilled artisan depending upon the particular equipment utilized. The Stead's reagent is preferably utilized at ambient temperature although the reagent may be heated or cooled, if desired, as known to the skilled artisan.

The sample is electrolytically etched in the Stead's reagent bath for a time sufficient to clearly delineate the grain cells and grain boundaries of the phosphorus-containing gray iron sample, which etching time is generally about 90 seconds or less, preferably about 60 seconds or less, most preferably about 30 seconds. The time of etching depends in part upon the alloy constituents present in a particular gray iron, such as, for example, manganese, nickel, chromium or molybdenum.

Generally, the sample will be immersed in the Stead's reagent and electrolytically etched for 30 seconds. The sample surface is then visually observed to determine if sufficient grain cell and grain boundary delineation has been achieved. If the sample does not show sufficient delineation, it is immersed again in the Stead's reagent and electrolytically etched for a time of up to 90 seconds, if necessary, generally with visual observation at 15 second immersion intervals.

As used herein, macroscopic examination is generally referred to as examination by the unaided eye or with the aid of a low power microscope usually under 15 X. Microscopic examination generally refers to magnifications generally in excess of 15 X, e.g., about 100 or more.

When etching has progressed for a time appropriate to produce a satisfactorily etched surface, the specimen is washed, for example, in a stream of warm running water to stop the action of the etching reagent and thoroughly remove from the specimen surface all traces of reagent. The specimen is then rinsed in ethyl or isopropyl alcohol to remove water droplets, and subsequently dried in a stream of warm air.

The following example is given as specific illustration of the claimed invention. It should be understood, however, that the invention is not limited to the specific details set forth in the example.

EXAMPLE

Various samples (all about ½"×⅜"×¾" in size) of gray iron are polished in a conventional manner and subjected to electrolytic etching as follows:

A bath of Stead's reagent is prepared by dissolving 10 gm cupric chloride, and 50 gm magnesium chloride in 10 to 15 ml of warm water and then adding 20 ml of hydrochloric acid and 1000 ml of methanol. The Stead's reagent is utilized as the electrolyte in a conventional electrolytic etching apparatus in which the specimen is adapted to be the anode, a platinum electrode is the cathode and the electrodes are connected to a standard 6 volt dry cell battery.

Gray iron samples are utilized containig various amounts of phosphorus of from about 0.05 weight percent up to about 0.60 weight percent phosphorus as well as one gray iron containing 1.2 weight percent phosphorus. Each of the samples is electrolytically etched in the Stead's reagent for 30 seconds and then macroscopically and microscopically observed for estimated grain size and grain cell count. The same samples are repolished and chemically etched in Stead's reagent in a conventional manner for 3 minutes and then macroscopically and microscopically observed for estimated grain size and grain cell count. The samples which are electrolytically etched in the Stead's reagent are sufficiently etched to show grain cell size and count values in 90% of the samples while sufficient resolution to obtain grain cell size and count values is obtained with only 25% of the samples which are chemically etched in the Stead's reagent.

Although the invention has been described with preferred embodiments, it is to be understood that variations and modifications may be resorted to as will be apparent to those skilled in the art. Such variations and modifications are to be considered within the purview and the scope of the claims appended hereto.

What is claimed is:
1. A process for electrolytically etching phosphorus bearing gray irons which comprises
   a. immersing a phorphorus-containing gray iron sample in a bath of Stead's reagent, and
   b. passing a direct current through said bath between said sample and a cooperating electrode to electrolytically etch the surface of the sample sufficient for microscopic or mascroscopic examination thereon.
2. The process of claim 1 wherein the sample is etched for a period of up to about 90 seconds.
3. The process of claim 2 wherein the sample is etched for a period of from 30 to 60 seconds.
4. In a process of electrolytically etching phosphorus bearing gray irons to reveal surface structure with an electrolytic reagent, the improvement comprising utilizing Stead's reagent as the electrolytic reagent.
5. In the process of claim 4, the improvement wherein said gray irons are etched for 60 seconds or less.
6. In the process of claim 5, the improvement wherein said gray irons contain up to about 1 weight percent phosphorus.
7. In the process of claim 4, the improvement wherein said gray irons contain up to about 0.60 weight percent phosphorus and said gray irons are etched for 30 seconds.

* * * * *